United States Patent
Casterlin et al.

(10) Patent No.: US 9,851,348 B2
(45) Date of Patent: Dec. 26, 2017

(54) SYSTEM AND METHOD FOR LATERAL FLOW IMMUNOASSAY TESTING

(71) Applicant: AMERICAN BIO MEDICA CORPORATION, Kinderhook, NY (US)

(72) Inventors: Douglas Casterlin, Hillsdale, NY (US); Larry Ferringo, Turnersville, NJ (US); Ian Sullivan, Kinderhook, NY (US); Rob Bernstine, Kinderhook, NY (US); Rich Reilly, Kinderhook, NY (US); Pablo Arroyo, Kinderhook, NY (US); Stan Cipkowski, Troy, NY (US)

(73) Assignee: AMERICAN BIO MEDICA CORPORATION, Kinderhook, NY (US)

( * ) Notice: Subject to any disclaimer, the term of this patent is extended or adjusted under 35 U.S.C. 154(b) by 34 days.

(21) Appl. No.: 14/205,631

(22) Filed: Mar. 12, 2014

(65) Prior Publication Data

US 2015/0260708 A1 Sep. 17, 2015

(51) Int. Cl.
G01N 33/543 (2006.01)
G01N 33/53 (2006.01)
G01N 33/558 (2006.01)

(52) U.S. Cl.
CPC ... *G01N 33/5304* (2013.01); *G01N 33/54366* (2013.01); *G01N 33/558* (2013.01)

(58) Field of Classification Search
None
See application file for complete search history.

(56) References Cited

U.S. PATENT DOCUMENTS

| | | |
|---|---|---|
| 6,464,939 B1 | 10/2002 | Bachand et al. |
| 7,090,803 B1 | 8/2006 | Gould et al. |
| 2004/0237674 A1 | 12/2004 | Wu et al. |
| 2006/0018800 A1 | 1/2006 | Slowey et al. |
| 2006/0275922 A1 | 12/2006 | Gould et al. |
| 2006/0292034 A1 | 12/2006 | Gould et al. |
| 2006/0292035 A1 | 12/2006 | Gould et al. |
| 2007/0128070 A1 | 6/2007 | Wu et al. |
| 2008/0076169 A1 | 3/2008 | Miles et al. |

(Continued)

OTHER PUBLICATIONS

International Search Report dated May 29, 2015 in PCT/US2015/019877.

(Continued)

*Primary Examiner* — Rebecca Martinez
(74) *Attorney, Agent, or Firm* — B. Aaron Schulman, Esq.; Stites & Harbison, PLLC

(57) ABSTRACT

A lateral flow immunoassay system is provided that includes a housing having a base portion forming a first chamber therein and a body portion formed with three openings in fluid communication with the first chamber, a vial containing a buffer agent, and a sample collector for introducing a sample fluid into the first chamber via the second opening. The vial is mounted to the housing such that a dispensing side extends into the first opening for dispensing the buffer agent therefrom into the first chamber. The housing allows the buffer agent and sample fluid to be mixed within a reaction well formed within the first chamber to form a test sample mixture. The body portion is configured to receive a receiving end of an elongated holder in the third opening and allow a test strip secured in the holder to be brought into communication with the text sample mixture.

14 Claims, 10 Drawing Sheets

(56) References Cited

U.S. PATENT DOCUMENTS

2010/0024530 A1   2/2010   Hopkins
2013/0157381 A1   6/2013   Pang et al.
2015/0030504 A1   1/2015   Pang et al.

OTHER PUBLICATIONS

International Preliminary Report on Patentabily dated Sep. 22, 2016 in PCT/US2015/019877.
Supplementary European Search Report dated Aug. 23, 2017 in EP 15 76 0993.
A M ABMC: Oralstat Quick Reference Guide, Dec. 31, 2008, pp. 1-1, XP055400724, Retrieved from the Internet: URL: http://www.abmc.com/products/documents/QRG_OralStat.pdf.

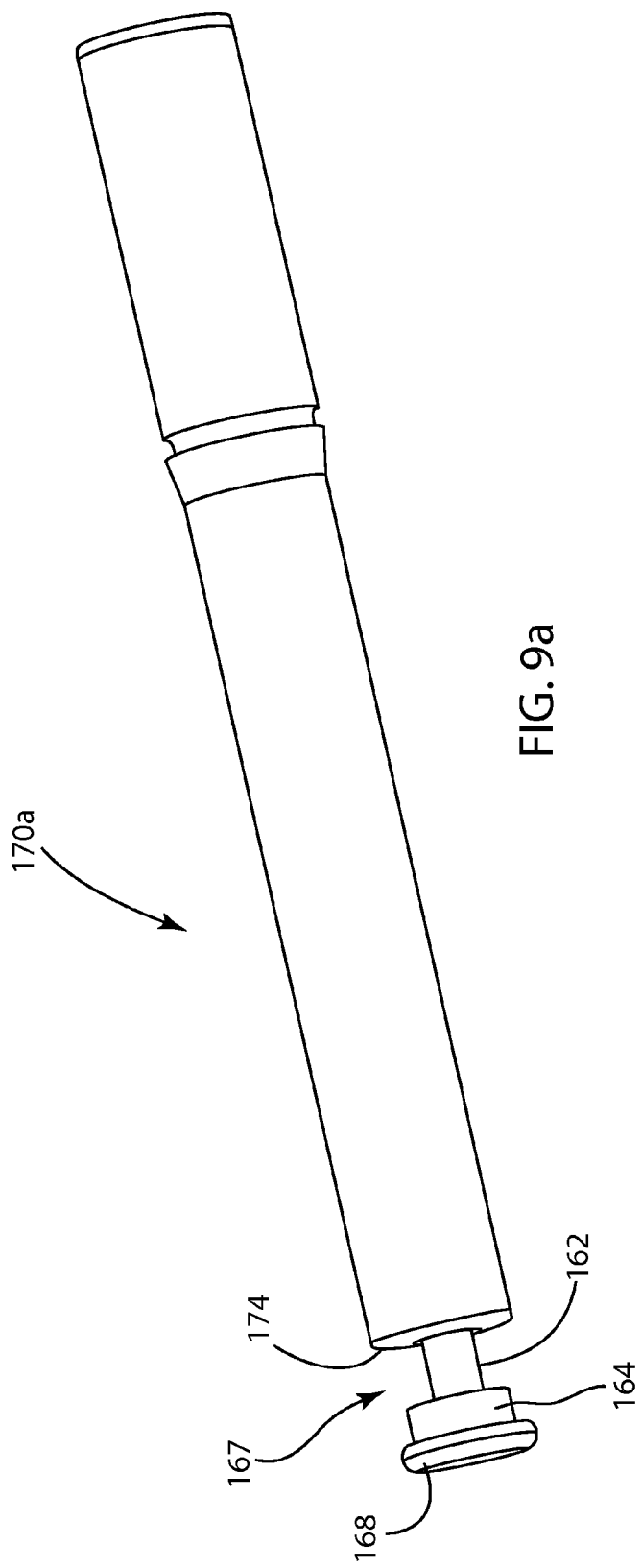

SYSTEM AND METHOD FOR LATERAL FLOW IMMUNOASSAY TESTING

BACKGROUND OF THE INVENTION

Exemplary embodiments of the present invention relate generally to point-of-care screening tests of body fluids such as saliva, blood, and other fluids for analytes including drugs of abuse and other compounds and materials. More specifically, exemplary embodiments relate screening tests for body fluids that require a test sample to be treated and incubated for a desired period of time prior to being introduced to an immunoassay test strip.

The increased availability and use of drugs of abuse along with the need for testing of other analytical targets ("analytes"), for example HIV or antibodies thereto, has caused employers, governmental agencies, sports groups, hospital emergency rooms, and other organizations to utilize drug and analyte screening methods in a wide variety of situations such as in screening individuals for potential employment or purchasing insurance, or to maintain safety in the work place. Screening tests for the detection of drugs of abuse and other analytes range in complexity from very complex analytical procedures to simple immunoassay tests. For example, while simple, preliminary drug screening tests are typically performed for the purpose of quickly identifying on a qualitative basis, the presence of drugs in a body fluid such as urine or saliva, a complete analysis of the sample may then be carried out in a laboratory if the preliminary screening results are positive.

More and more such drug screenings are taking place on site, for example at the workplace or during routine police stops or check points. Thus, in settings such as law enforcement, there is a constant need for providing improved on-the-spot testing for drugs of abuse or other analytes in a quick and simple manner since initial tests will be far removed from the clinical setting. Such on-the-spot testing is facilitated through the use of point-of-care (POC) testing devices. The term "POC" encompasses many possible end-use settings outside of a centralized testing facility, ranging from regional health clinics and physicians' offices to emergency settings and other resource limited settings such at-home or mobile use. Such testing devices are designed accept a sample with relatively little or no pre-preparation, test for one or more analytical targets, and provide a result, which can be interpreted in a simple manner to provide the "answer", in seconds to hours. The analytes of such tests can include proteins, nucleic acids, metabolites, drugs, dissolved ions and gases, human cells, and microbes. Samples may include blood, saliva, urine, or other bodily fluids or (semi) solids.

Thus, POC testing devices can provide results rapidly, where needed, as samples do not travel to a laboratory to await the attention of a skilled technician. Results do not wait to be transmitted and collected; rather, the user initiates the test and receives the results on the spot. Inevitably this saves time, but as these tests are typically carried out by testing personnel who are generally not technically trained as would be a laboratory technician, the lack of professional control and the potential for incorrect interpretation of results leads to concerns that accuracy or reliability are being traded for speed. It is thus important that the drug screening procedure be simple yet reliable and that the testing apparatus be designed so as to enable the testing personnel to avoid all contact with the fluid specimen which is being tested.

Over the years the speed and specificity of immunoassays have made them one of the most accepted methods for screening for drugs of abuse in body fluids. Immunoassay is accomplished in minutes to an hour or more (depending on incubation times). A major class of immunoassay POC testing is the lateral flow test, which uses a membrane or paper strip to indicate the presence of protein markers such as pathogen antigens or host antibodies. On a membrane, addition of sample induces capillary action without user intervention (leveraging capillary forces for fluid actuation). As the sample flows across the membrane, it gathers labeling reagents embedded in the membrane, and flows over an area that contains capture molecules; the labeled captured analytes are interpreted by eye to form a visible band. In the U.S., lateral flow tests are most notably used for pregnancy testing, screening for infectious diseases and drugs of abuse, and for measurement of protein markers in blood to aid rapid clinical diagnostics of life-threatening events such as heart attack, stroke, and deep-vein thrombosis. In developing countries, the lateral flow test is widely used to diagnose HIV.

The large investment in lateral flow devices has resulted in significant interest in trying to improve their performance in producing highly reproducible, quantitative, and sensitive results. Although the test may be simple to perform using a lateral flow device, difficulties of measurement can arise because the unit operations (particularly mixing, incubation timing, sample normalization, and rinsing) may not be as well controlled as in a laboratory machine. Efforts to address the critical issues of error and accuracy have targeted control of the sample volume into which the label is dispersed, uniformity of dispersion, and flow rate, which is the main determinant of contact and incubation times.

While blood and urine samples have long been the primary fluids used for testing for disease as well as for evidence of substance abuse, there is increasing interest in testing regimens which can test a variety of body fluids including salivary specimens. Some advantages in a system that can test saliva in addition to bodily fluids more traditionally used in testing are that it is relatively easy to obtain a saliva sample and that a saliva sample obtained on the spot cannot be adulterated. Also, saliva testing is more suitable in testing of recent use since it does not maintain reactivity of the analyte after use for up to four to six weeks. Accordingly, testing of saliva gives a result in real time within a span of hours as compared to urine which gives a test result after-the-fact. In general, saliva and blood are useful to measure impairment, while urine tests generally are not suitable for this purpose.

Nevertheless, the ability to collect and analyze saliva samples in addition to other bodily fluids using an immunoassay for diagnostic purposes is complicated by the relatively high viscosity of the fluid and the small volumes of salivary fluid secreted. In particular, saliva contains mucins, which are a family of large, heavily glycosylated proteins that account for many of the properties of saliva. These mucins also act to disrupt or inhibit the lateral flow necessary to achieve a rapid and accurate test result and considerably restrict the time it takes for a sample to travel through the immunoassay strip as well as the amount of the target compound in the sample which can travel up the strip and thus be measured by the immunoassay.

Because of the problems caused by mucins, certain testing systems have recommended long and elaborate procedures for removing mucins prior to testing the sample. These procedures include pre-treating a sample such as saliva with a diluent or other reagent which is capable of breaking down the interferants in a sample, e.g., mucins in saliva, so that these interferants do not restrict the capillary flow of the sample through the test strip, in order to try to achieve a rapid test of target compounds. However, these pre-treatment steps with specific reagents to dilute or denature interferants, modify analyte structure, or release analyte from binders must generally be performed outside the confines of the test device. This requires persons administering the test to take additional steps and handle additional solutions. For example, it is necessary to suitably collect the sample, have the sample expressed into a buffer solution, and then have the expressed sample dispensed into a reaction well, which typically contains a second reagent such as an identifying reagent, all prior to introducing the testing solution including the sample onto an immunoassay test strip. All these steps necessitate the development of means and techniques for constructing self-contained devices which can test for saliva in addition to other body fluids in a manner that allows one to safely and efficiently control the test sample during pre-treatment and testing while remaining simple to use and providing the ability to obtain accurate results.

SUMMARY OF THE INVENTION

Exemplary embodiments of the present invention are related to a lateral flow immunoassay system that includes a housing that includes a base portion having a first chamber formed within an interior of the base portion and a reaction well formed within the first chamber and a body portion formed with first, second, and third openings in fluid communication with the first chamber, a vial mounted to the body portion such that the vial is in fluid communication with the first chamber via the first opening of the housing, and a sample collector comprising a stem and an absorbent retained on a distal end of the stem. The reaction well is located beneath and in fluid communication with the second and third openings. The vial is configured to dispense a buffer agent contained therein into the first chamber. The base portion is configured to, in response to the buffer agent being dispensed from the vial into the first chamber, direct the buffer agent to the reaction well. The sample collector is configured to be inserted from the distal end into the housing such that the distal end extends through the second opening to dispose the absorbent within the reaction well of the first chamber. The sample collector is configured to introduce a sample fluid absorbed within the absorbent to the reaction well upon the sample collector being inserted in the housing. The housing, upon the buffer agent being dispensed from the vial and directed to the reaction well and the sample fluid being introduced to the reaction well, allows for the buffer agent and the sample fluid to be mixed within the reaction well to form a test sample mixture within which the absorbent is immersed. The body portion is configured to receive a sample receiving end of an elongated holder member securing at least one immunoassay test strip therein in the third opening and support the holder member to allow for the test strip to be brought into communication with the text sample mixture upon the test sample mixture being formed within the reaction well.

Exemplary embodiments of the present invention are also related to a lateral flow immunoassay system that includes a housing with a base portion having a first chamber formed within an interior of the base portion and body portion formed with first, second, and third openings in fluid communication with the first chamber, a vial containing a buffer agent therein and mounted to the housing such that a dispensing side of the vial extends into the first opening of the body portion from an exterior of the housing to be in fluid communication with the first chamber, and a sample collector configured to introduce a sample fluid into the first chamber via the second opening of the housing. The vial is configured to dispense the buffer agent from the dispensing side into the first chamber in response to a compressing force being exerted on an exterior surface of the vial. The housing, upon the buffer agent being dispensed from the vial and the sample fluid being introduced to the first chamber, allows for the buffer agent and the sample fluid to be mixed within a reaction well formed within the first chamber of the base portion to form a test sample mixture therein. The body portion is configured to receive a sample receiving end of an elongated holder member securing at least one immunoassay test strip therein in the third opening and support the holder member to allow for the test strip to be brought into communication with the text sample mixture upon the test sample mixture being formed within the reaction well.

Exemplary embodiments of the present invention are also related to a method for testing a sample fluid. The method includes providing a housing that includes a base portion having a first chamber formed within an interior of the base portion and a reaction well formed within the first chamber, a body portion formed with a first opening in fluid communication with the first chamber and second and third openings located above and in fluid communication with the reaction well within the first chamber, and a vial mounted to the body portion such that the vial is in fluid communication with the first chamber via the first opening of the housing, dispensing a pre-treatment reagent contained within the vial into the first chamber via the first opening, directing the pre-treatment reagent dispensed into the first chamber from the vial to the reaction well, receiving an absorbent in the reaction well of the first chamber via the second opening such that the absorbent is disposed within the reaction well in contact with the pre-treatment reagent, introducing a sample fluid absorbed within the absorbent disposed within the reaction well to the reaction well, allowing for the pre-treatment reagent dispensed from the vial and the sample fluid introduced to the reaction well from the sample collector to be mixed within the reaction well to form a test sample mixture within which the absorbent is immersed, and receiving a sample receiving end of an elongated holder member securing at least one immunoassay test strip therein in the reaction well via the third opening of the body portion to bring the test strip into communication with the text sample mixture and initiate a test of the sample fluid.

Exemplary embodiments of the present invention are also related to a method for testing a sample fluid. The method includes providing a housing that includes a base portion having a first chamber formed within an interior of the base portion, a body portion formed with first, second, and third openings in fluid communication with the first chamber, and a vial containing a buffer agent therein and mounted to the body portion such that a dispensing side of the vial is in fluid communication with the first chamber via the first opening of the housing, exerting a compressing force on an exterior of the vial to dispense the buffer agent from the dispensing side into the first chamber, introducing a sample fluid from a sample collector into the first chamber via the second opening of the housing, allowing for the buffer solution dispensed from the vial and the sample fluid introduced to the first chamber to be mixed within a reaction well formed within the first chamber to form a test sample mixture therein, and receiving a sample receiving end of an elongated holder member securing at least one immunoassay test strip therein in the reaction well via the third opening of the body portion to bring the test strip into communication with the text sample mixture and initiate a test of the sample fluid.

The above-described and other features and advantages of the present disclosure will be better appreciated and understood by those skilled in the art with reference to the following detailed description, drawings, and appended claims. Additional features and advantages are realized through the techniques of the present invention. Other embodiments and aspects of the invention are described in detail herein and are considered a part of the claimed invention.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description of exemplary embodiments of the present invention taken in conjunction with the accompanying drawings in which:

FIG. 9a is a side view illustrating an exterior of a portion of a sample collector in accordance with an exemplary embodiment of the present invention; and FIG. 9b is a side view illustrating an interior of a portion of the exemplary sample collector of FIG. 9a.

Figure 1:
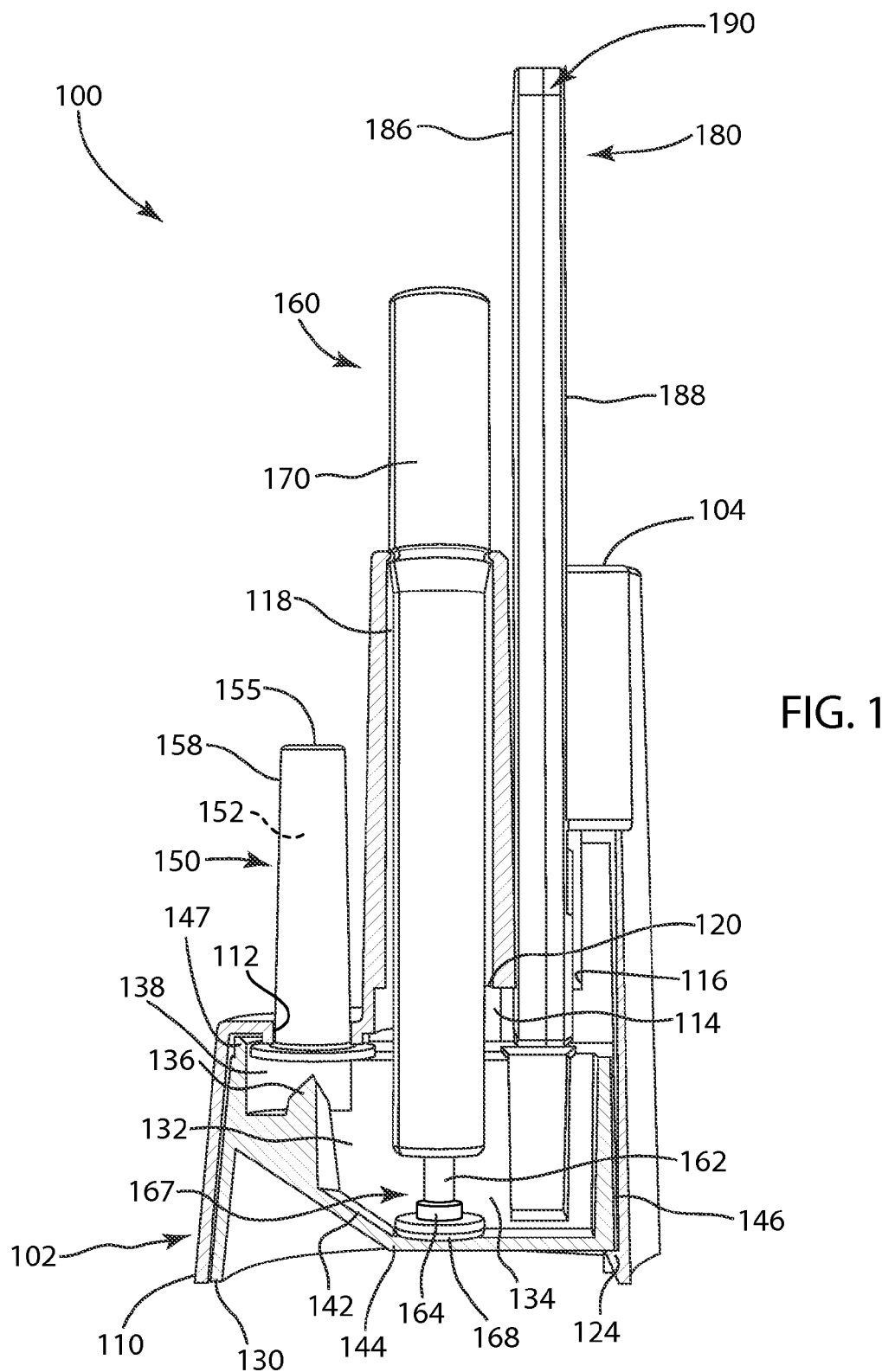
FIG. 1 is a first side view illustrating a lateral flow immunoassay testing system in accordance with an exemplary embodiment of the present invention in which a housing of the exemplary testing system is depicted using an open, cross-sectional view to show an interior of the housing.
Figure 2:
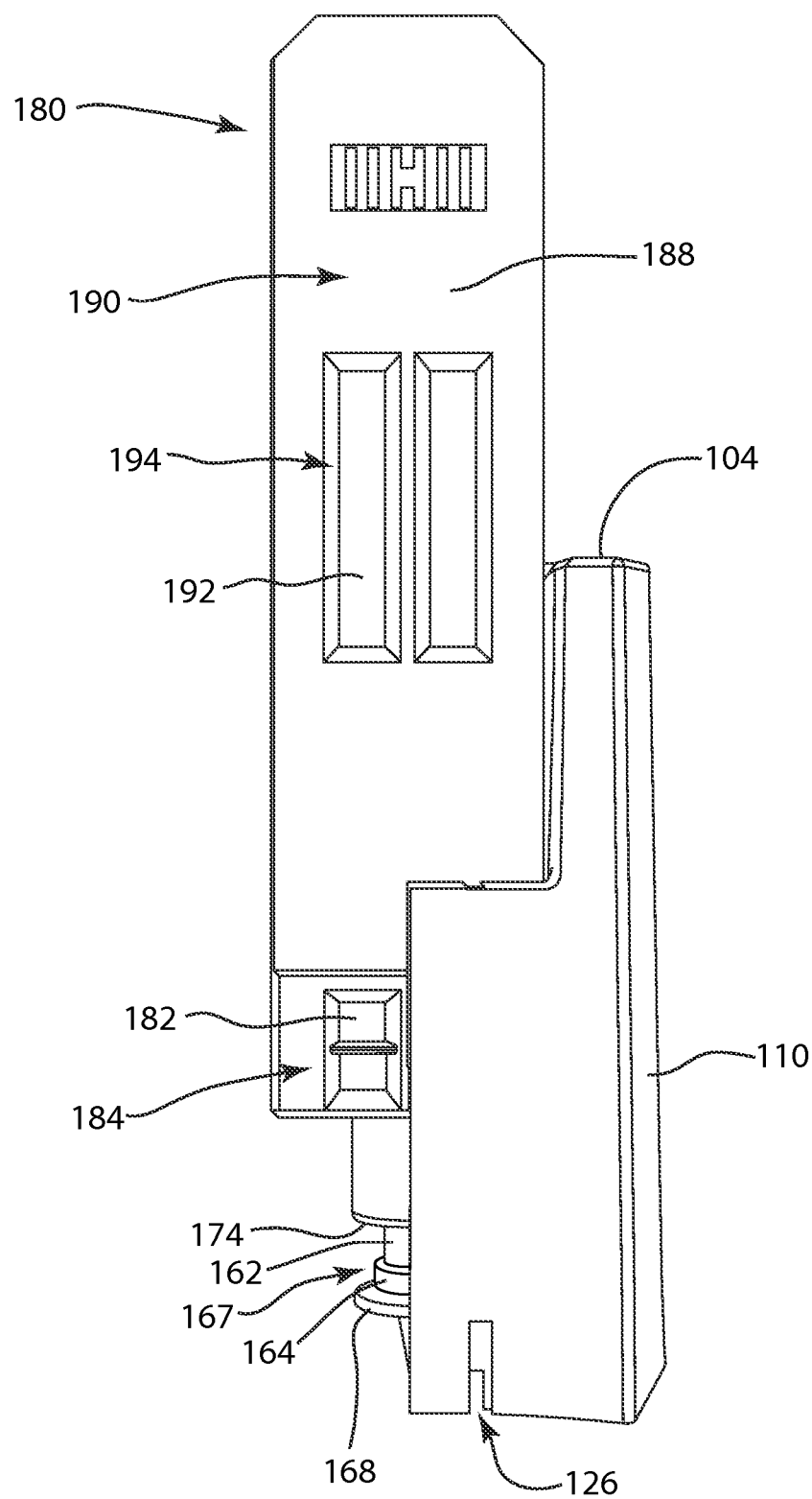
FIG. 2 is a second side view illustrating the exemplary testing system of FIG. 1 in which the housing of the exemplary testing system is depicted in cross-sectional form along the same cross-sectional plane as in FIG. 1.
Figure 3:
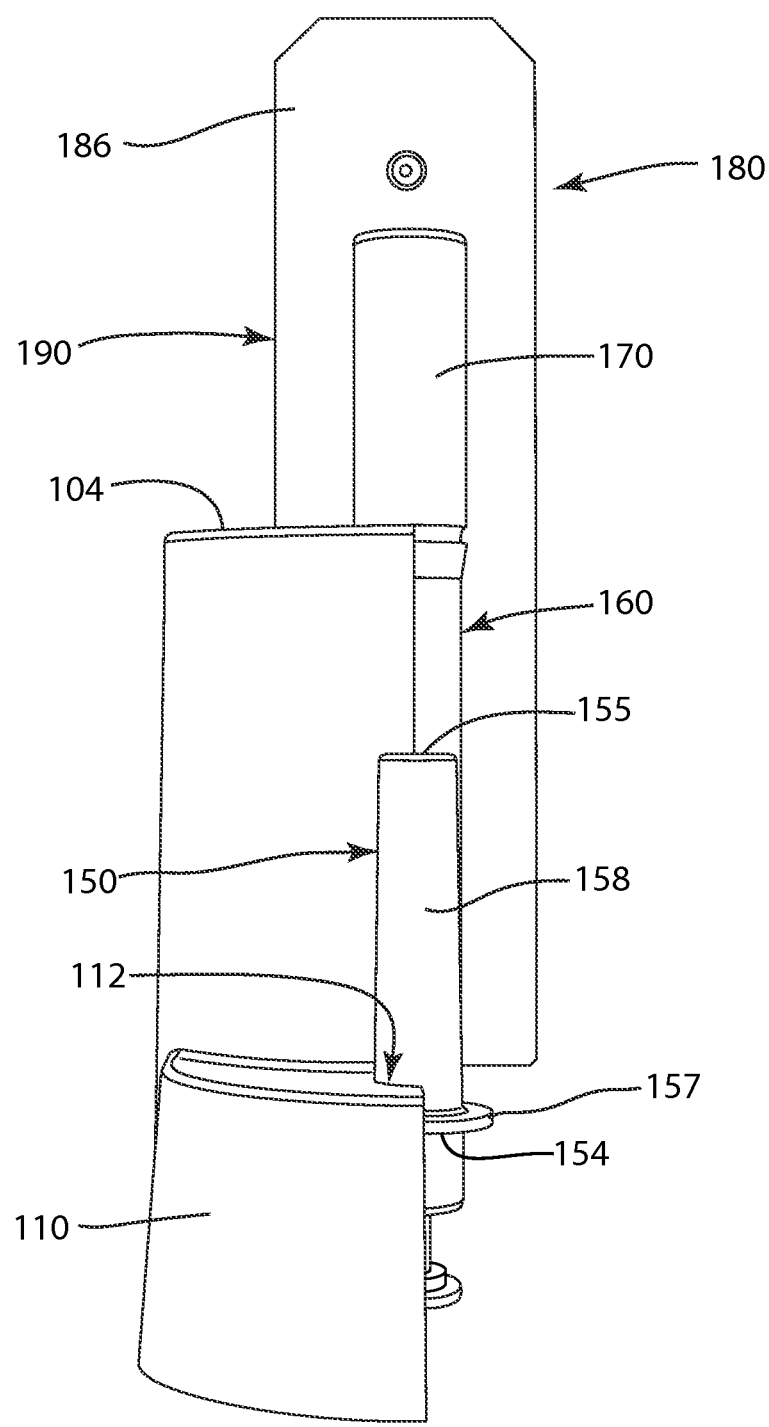
FIG. 3 is a third side view illustrating the exemplary testing system of FIG. 1 in which the housing of the exemplary testing system is depicted in cross-sectional form along the same cross-sectional plane as in FIG. 1.

The detailed description explains exemplary embodiments of the present invention, together with advantages and features, by way of example with reference to the drawings, in which similar numbers refer to similar parts throughout the drawings. The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered to be within the scope of the claimed invention.

DETAILED DESCRIPTION

While the specification concludes with claims defining the features of the invention that are regarded as novel, it is believed that the invention will be better understood from a consideration of the description of exemplary embodiments in conjunction with the drawings. It is of course to be understood that the embodiments described herein are merely exemplary of the invention, which can be embodied in various forms. Therefore, specific structural and functional details disclosed in relation to the exemplary embodiments described herein are not to be interpreted as limiting, but merely as a representative basis for teaching one skilled in the art to variously employ the present invention in virtually any appropriate form, and it will be apparent to those skilled in the art that the present invention may be practiced without certain specific details. Further, the terms and phrases used herein are not intended to be limiting but rather to provide an understandable description of the invention. As used herein, the singular forms "a", "an", and "the" are intended to include the plural forms as well, unless the content clearly indicates otherwise. It will be further understood that the terms "comprises", "includes", and "comprising", when used in this specification, specify the presence of stated features, integers, steps, operations, elements, components, and/or groups thereof.

Exemplary embodiments of the present method can be implemented to provide a safe and effective mechanism for performing a quick and accurate test for analytes such as drugs of abuse from a variety of test sample body fluids, including saliva, in a quick and efficient manner. Exemplary embodiments can be implemented to facilitate proper treatment and incubation of the test sample prior to being introduced to a test strip and provide for ready access to a reaction well for the test sample, which is then contacted by a test strip. Exemplary embodiments can be implemented to provide body fluid testing devices that are particularly adapted to receive a sample, extract the sample by treating it with a buffer, and ultimately introduce the sample to an identifying reagent which allows for qualitative, quantitative, or semi-quantitative identification of the drugs of abuse or other analytes in the sample, while facilitating precise control of the sample fluid, buffer, and reagent flow and delivery.

Exemplary embodiments of the present invention can be implemented to provide mechanisms for testing for analytes in a variety of collectable body fluids, including fluids such as saliva, blood, urine, cerebrospinal fluid, nasal fluid, buccal cavity scrape/swab, tears, sweat, vaginal secretions, ear wax, and other bodily fluids. Exemplary embodiments can provide for testing for a variety of analytes, that is, constituents or materials which can be detected or measured from the body fluid of a subject, and such analytes include drugs of abuse, chemical compounds such as glucose, insulin, proteins, bilirubin, urobilinogen, ketones, and other biological materials, for example, viral particles such as HIV and leukocytes. With regard to drugs of abuse, exemplary embodiments can be implemented to provide for testing of any suitable drug, including but not limited to amphetamines, benzodiazepines, cocaine, methadone, methamphetamines, opiates, phencyclidine (PCP), barbituates, buprenorphine, mdma, oxycodone, tricyclic antidepressants and THC (in either its parent form or metabolite form).

Referring now to FIGS. 1-6, various views illustrating an exemplary embodiment of a lateral flow immunoassay testing system 100 in accordance with the present invention are provided. Initially, it should of course be understood that the system and the various components thereof illustrated in the drawings are intended as examples, not as any structural limitations for different embodiments of the present invention, and therefore, the particular structure and elements of the system depicted in the drawings should not be considered limiting with regard to the present invention. As illustrated in FIG. 1, exemplary testing system 100 generally includes a housing 102 having a body portion 110 and a hollow base portion 130, a buffer vial 150, a sample collector 160, and an elongated immunoassay test strip holder 180 that support at least one immunoassay test strip 182 therein in a vertical position.

In the present exemplary embodiment, a mixing chamber 132 is formed within an interior of base portion 130 of housing 102, and a reaction well 134 is formed within the mixing chamber. Body portion 110 is formed with first, second, and third openings 112, 114, 116, each of which is in fluid communication with mixing chamber 132. Second opening 114 is transversely interposed between first and third openings 112, 116 in the body portion, and reaction well 134 is located beneath and in fluid communication with second and third openings 114, 116. Buffer vial 150 is mounted to body portion 110 via first opening 112, housing 102 is configured to receive via second opening 114 such that a distal end 167 of the sample collector extends through the second opening and into reaction well 134 of mixing chamber 132, and third opening 116 is configured as a slot for insertably receiving test strip holder 180 therein. In exemplary embodiments in which multiple test strips are utilized in testing procedures, such as for detecting the presence of more than one drug of abuse or analyte at the same time, base portion 130 can be configured to provide two or more separate reaction wells within housing 102 of testing device 100.

In the present exemplary embodiment, body portion 110 and base portion 130 are separate parts, and the body portion is configured to be detachably mounted on the base portion to thereby bring first, second, and third openings 112, 114, 116 in fluid communication with mixing chamber 132. Mixing chamber 132 is formed within base portion 130 by a bottom section 144 and one or more side walls 146 that vertically extend upward from the bottom section to in correspondence with a shape of the bottom section to thereby define an outer shape of the base portion and, in conjunction with the bottom section, the dimensions of the mixing chamber within the base portion.

Figure 7:
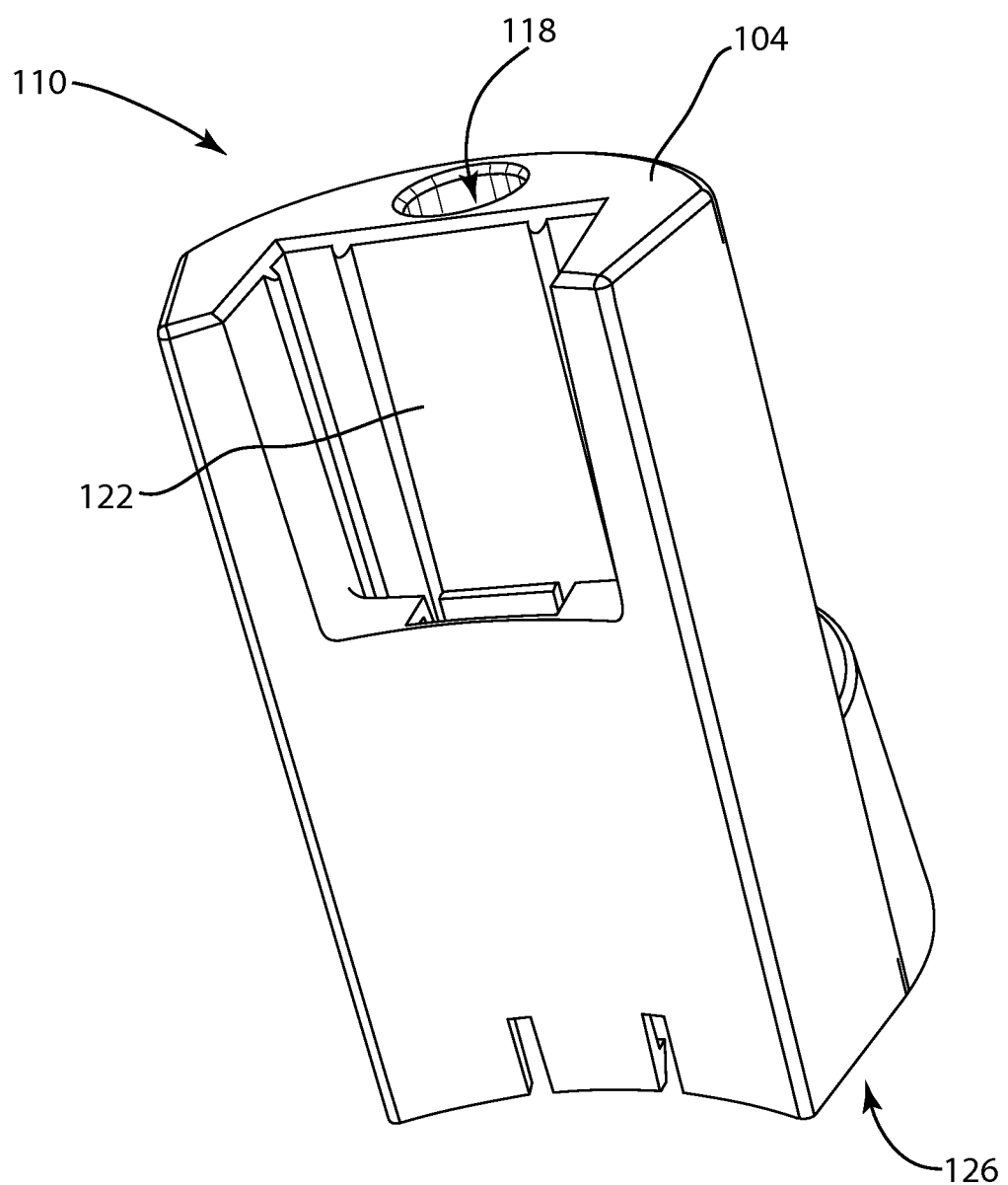
FIG. 7 is a side perspective view illustrating a body portion of the housing of the exemplary testing system of FIG. 1.
Figure 8:
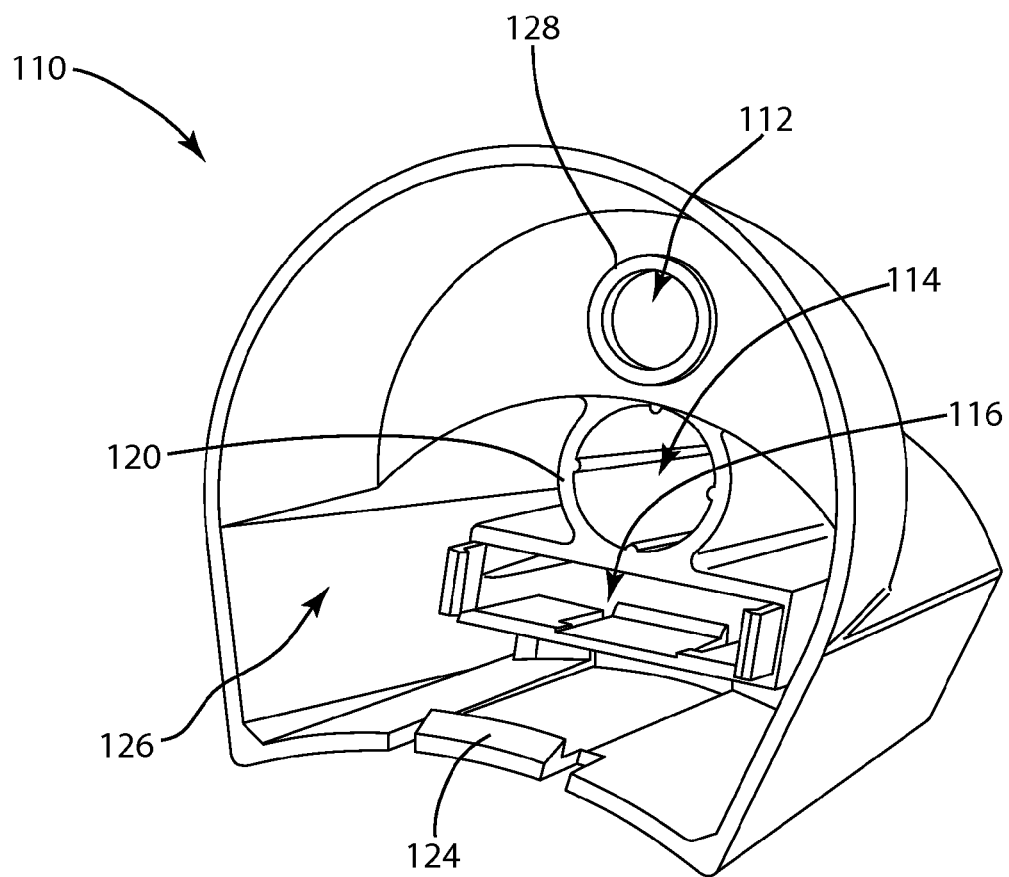
FIG. 8 is a side perspective view illustrating a body portion of the housing of the exemplary testing system of FIG. 1.

In the present exemplary embodiment, as illustrated in greater detail in FIGS. 7 and 8, body portion 110 is correspondingly formed as an open-ended casing extending downward from first, second, and third openings 112, 114, 116 such that an interior shape of the body portion is configured to conform to the outer shape of base portion 130 and thereby provide for the casing to be fitted closely about the exterior of base portion when the body portion is mounted on the base portion. When mounted on base portion 130, body portion 110 is retained thereon by way of a detachable snap fitting that is provided by way of an inwardly extending lip 124 on at least a portion of an open end 126 of the casing and a groove 148 formed on bottom section 144 of the base portion that is configured to catch the lip upon the open end of the casing being positioned above the base portion and brought downward about the exterior of the base portion to attach the body portion to the base portion.

In alternative exemplary embodiments, body portion 110 and base portion 130 may be integrated to form a one-piece housing. In exemplary embodiments, housing 102 may be made of any suitable material such as metal or thermoplastic material using, for instance, embossing or injection molding.

Figure 4:
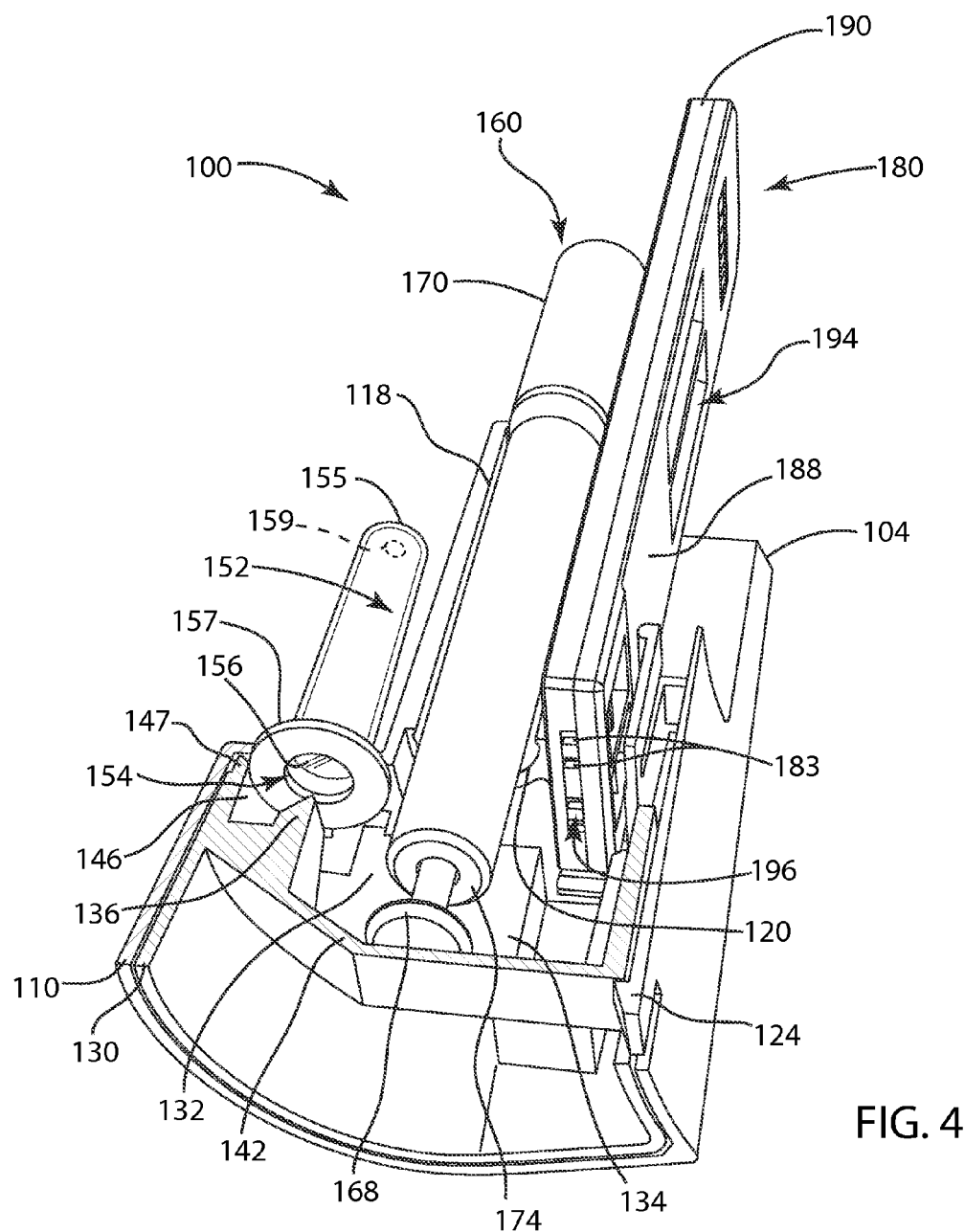
FIG. 4 is a first bottom perspective view illustrating the exemplary testing system of FIG. 1 in which the housing of the exemplary testing system is depicted using an open, cross-sectional view along the same cross-sectional plane as in FIG. 1.
Figure 5:
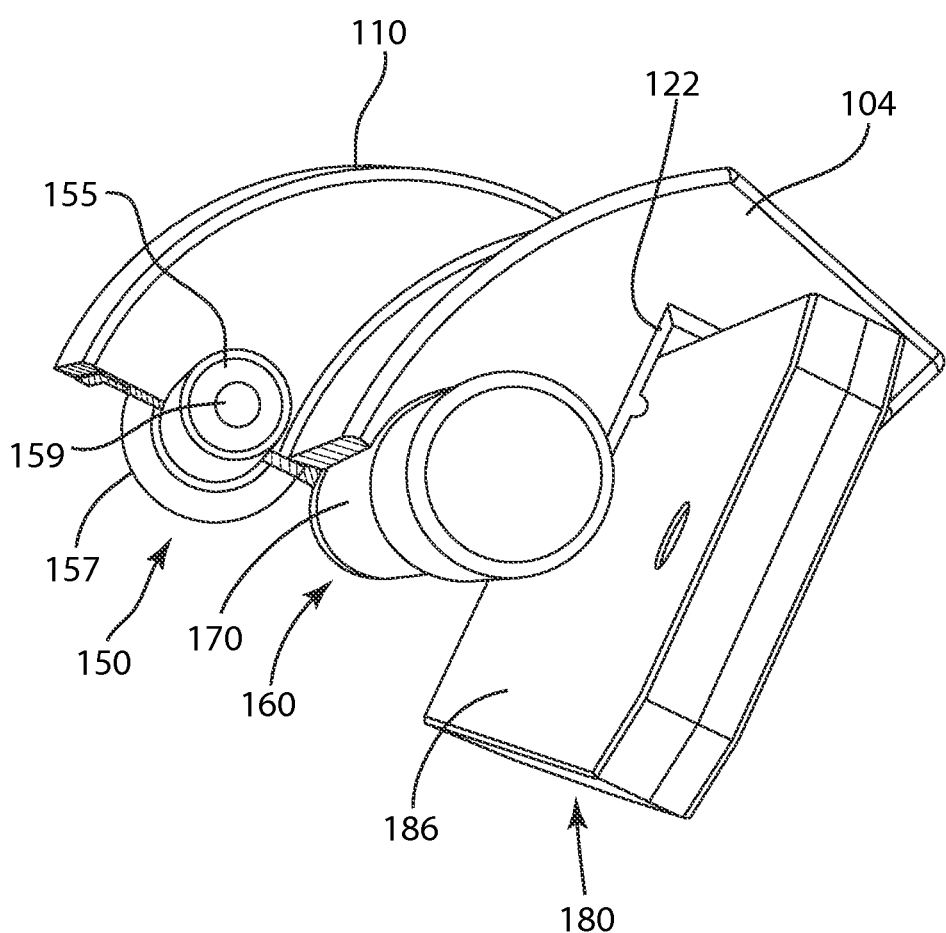
FIG. 5 is a top perspective view illustrating the exemplary testing system of FIG. 1 with the housing of the exemplary testing system being depicted in cross-sectional form along the same cross-sectional plane as in FIG. 1.
Figure 6:
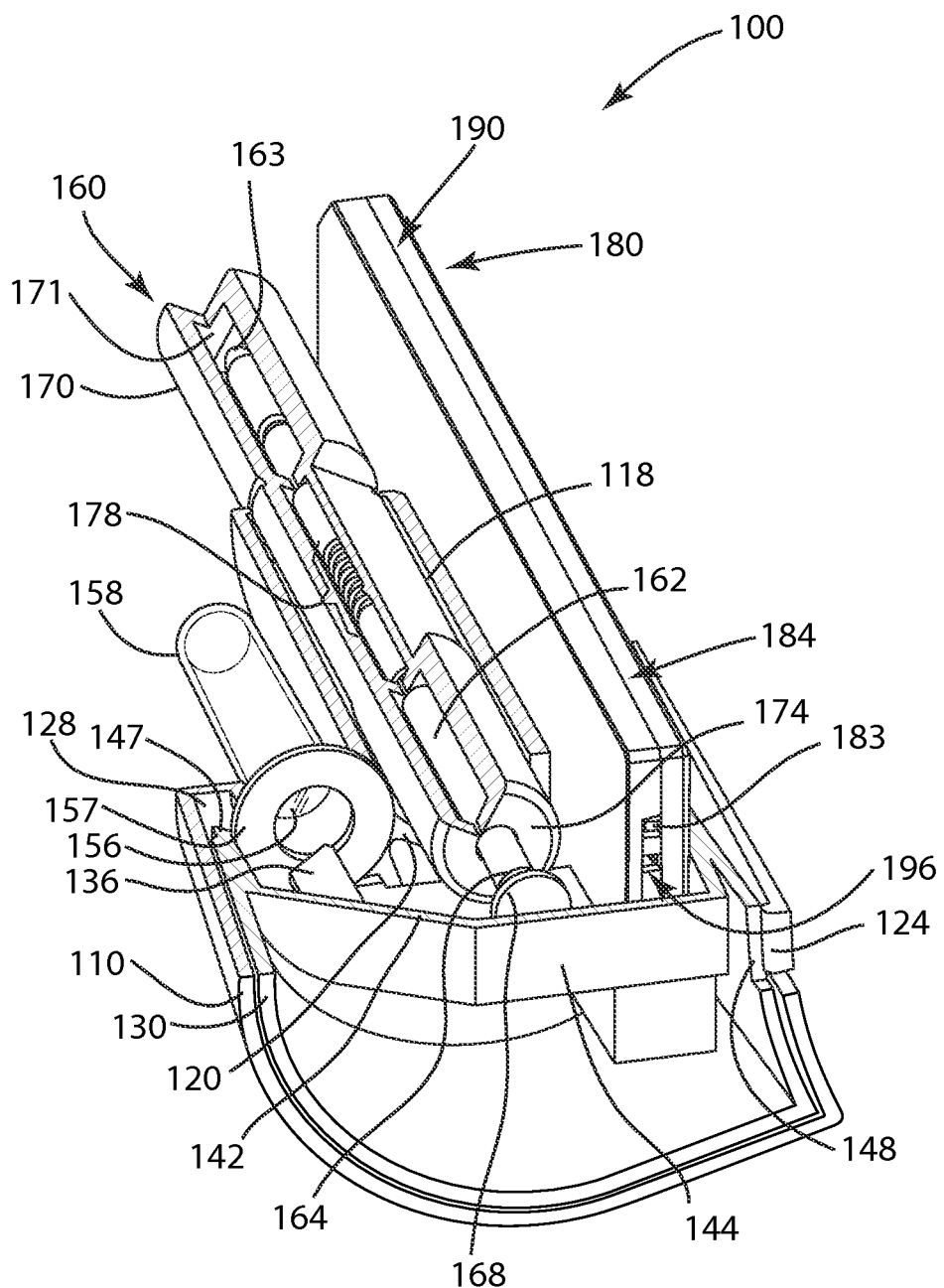
FIG. 6 is a second bottom perspective view illustrating the exemplary testing system of FIG. 1 in which the housing of the exemplary testing system is depicted using an open, cross-sectional view along the same cross-sectional plane as in FIG. 1.

As best illustrated in FIGS. 4-6, buffer vial 150 is formed as a cylindrical housing and mounted to body portion 110 such that the buffer vial is in fluid communication with mixing chamber 132 via first opening 112. Buffer vial 150 is configured to dispense a buffer agent 152 contained therein into mixing chamber 132. Buffer agent 152 will be utilized to prepare a test sample for immunological testing, such as by breaking down mucins when the sample being tested is saliva. In general, the use of buffer agent 152 will allow for a more sensitive test for the drug or other analyte of interest by removing interfering particles from the test sample and/or reducing the viscosity of the solution. For example, buffer agent 152 can be formulated to solubilize the analytes of interest, thereby making them available to react with the labeled antibodies in an immunoassay. In addition, buffer agent 152 can also be formulated to remove or denature interferants so as to improve the ability of the analyte to be detected in a lateral flow immunoassay, and, in the example in which the body fluid being tested is saliva, the buffer agent can promote the breakdown of mucins in the saliva sample and enhance the sensitivity of the immunoassay based on this saliva sample. Thus, in exemplary embodiments, buffer agent 152 can include reagents that are suitable for and capable of breaking down the interferants in a sample so that these interferants do not restrict the capillary flow of the test sample through test strip 182 to facilitate a rapid test of target compounds in an accurate manner. Buffer agent 152 may thus generally include specific reagents which can solubilize the analyte, dilute or denature interferants, modify analyte structure, and/or release analyte from binders so as to be utilized in pre-treatment steps as appropriate for the body fluid being tested.

In the present exemplary embodiment, to dispense buffer agent 152, buffer vial 150 is configured to, with a dispensing side can include reagents of the buffer vial mounted within first opening 112 of housing 102 and in fluid communication with mixing chamber 130, and upon an aperture being formed in the dispensing side, dispense buffer agent 152 through the aperture in the dispensing side into the mixing chamber in response to a compressing force being exerted on the buffer vial. In exemplary embodiments, to allow for exertion of the compressing force on the buffer vial to cause dispensing of buffer agent 152 through the aperture that is formed in dispensing side 154 of buffer vial 150, the buffer vial can be formed from a deformable material. For example, buffer vial 150 may be formed from a thermoplastic polymer such as polypropylene or polyethylene (such as low-density polyethylene) or a plastic foam material such as expanded polypropylene.

In exemplary embodiments of the present invention, a measured amount of buffer agent 152 can be contained in buffer vial 150, and the buffer vial can be configured to dispense a predetermined amount of buffer agent 152 into mixing chamber 132 in response to the compressing force being exerted on the exterior thereof in a manner that is precise and repeatable. For example, the buffer vial 150 is can be formed from a deformable material that possesses a modulus of elasticity that is determined to cause the vial to deform elastically in a predetermined manner that causes dispensing of a predetermined amount of buffer agent 152 into mixing chamber 132 in response to a corresponding level of compressing force being exerted on the exterior of the buffer vial. In exemplary embodiments, buffer vial 150 is provided as a graduated bottle that indicates a total volume of buffer agent 152 included therein to aid in quantification or semi-quantification of the amount of the buffer agent dispensed during the testing procedure. For example, buffer vial 150 can be designed to provide for quantification in terms of weight and/or volume to facilitate measurements in terms of weight/weight or volume/volume.

As illustrated in FIGS. 1, 4, and 6, an upwardly directed spike or piercing member 136 that protrudes from a bottom end thereof from an inner surface 138 of base portion 130 within mixing chamber 132 and has a tip at a top end thereof that is in a facing spaced relationship with first opening 112. Housing 102 is configured to hold buffer vial 150 within first opening 112 at a position spaced apart from piercing member 136 within mixing chamber 132 and to allow for a depressing force exerted on the buffer vial to move the vial downward through the first opening to engage a pierceable or rupturable material of an end surface 156 closing the buffer vial at dispensing side 154 thereof with the piercing member and thereby form the aperture in the rupturable end surface of the buffer vial.

More specifically, buffer vial 150 includes an annular member 157 that extends about end surface 156 at dispensing side 154, and base portion 130 includes a tab 147 protruding from a surface of inner side wall 146 below first opening 112. Housing 102 is thereby configured to retain buffer vial 150 in the first position spaced apart from the piercing member through engagement of annular member 157 with tab 147 such that a portion of the annular member is supported between the tab and an upper inner surface 128 of body portion 110 proximate to first opening 112. Moreover, housing 102 is also thereby configured so that the depressing force exerted on buffer vial 150 operates to push annular member 157 downward past tab 147 to allow for the vial to be moved downward through first opening 112 to engage end surface 156 with piercing member 136 and form the aperture through which buffer agent 152 is dispensed into mixing chamber 132 in response to the exertion of the compressing force on the buffer vial.

In the present exemplary embodiment, buffer vial 150 is mounted within housing 102 to allow for the depressing force to be manually exerted on a top surface 155 thereof that is opposite end surface 156 for moving the vial downward through first opening 112 and to allow for the compressing force to be manually exerted by a squeezing action on an exterior surface 158 of the buffer vial. For this purpose, buffer vial 150 includes a buffer button 159 protruding from top surface 155 that, upon being depressed, urges the buffer downward so thereby cause end surface 156 to rupture against piercing member 136. In alternative exemplary embodiments, housing 102 may configured to, in response to a button located on an exterior of body portion 110 being depressed, automatically exert the depressing force to move buffer vial 150 downward through first opening 112.

In another alternative exemplary embodiment, housing 102 may be further configured to convert downward motion of buffer vial 150 through first opening 112 into biaxial compression on exterior surface 158 of the buffer vial that acts as the compressing force on the exterior of the vial that causes the buffer vial to dispense buffer agent 152 from the aperture in dispensing side 154 downwardly into mixing chamber 132. For example, housing 102 can be further configured to provide a pair of triangular-shaped pivoting tabs with respective sides disposed along opposite sides of exterior surface 158 of buffer vial 150 that operate to pivot in response to downward motion of the buffer vial through the first opening (for example, while buffer button 159 is being depressed) such that respective top corner sections of the pivoting tabs progressively move farther inward against the respective sides of the exterior surface of the buffer vial as the tabs pivot to thereby apply a preconfigured amount of compressing force on the exterior of the vial that causes the buffer vial to dispense a predetermined amount of buffer agent 152 into mixing chamber 132.

Base portion 130 of housing 102 is configured to, in response to the buffer agent 152 being dispensed from buffer vial 150 into mixing chamber 132, direct the buffer agent to reaction well 134. More specifically, as depicted in FIGS. 1, 4, and 6, bottom section 144 of base portion 130 is formed with an inclined portion 142 below first opening 112 that slopes transversely beneath mixing chamber 132 toward reaction well 134 for, upon the buffer agent 152 dispensed from the vial into the mixing chamber, directing the buffer agent to descend by force of gravity down the inclined portion and thereby flow into the reaction well of the mixing chamber.

Figure 9B:
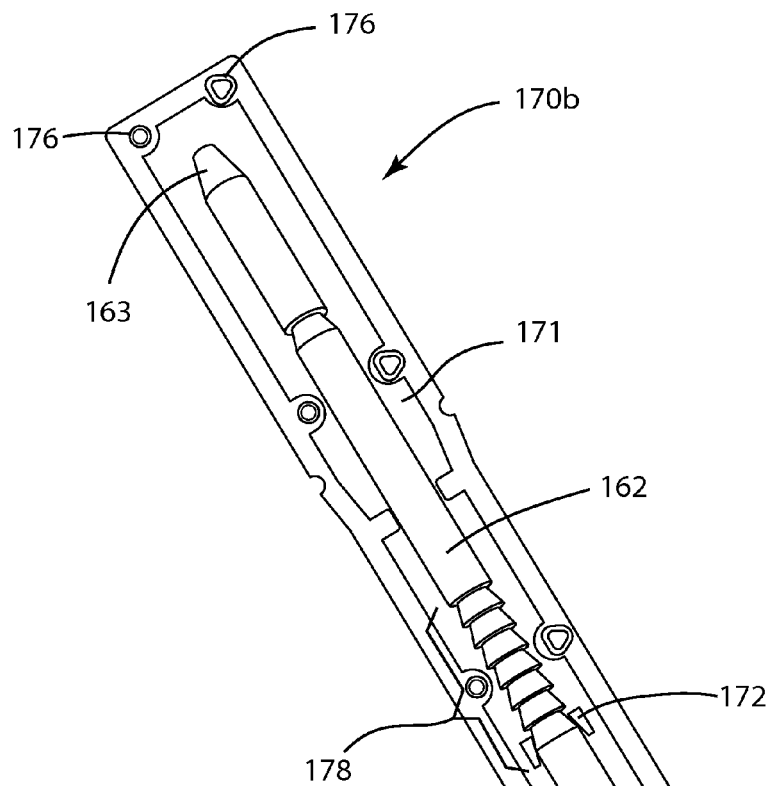

In the present exemplary embodiment, as illustrated in greater detail in FIGS. 9a and 9b, sample collector 160 includes an elongated stem 162 and an absorbent collector sponge 164 that is retained on distal end 167 of the stem. Stem 162, with absorbent 164 positioned thereon, is used in the collection of a body fluid sample from an individual to be tested. In exemplary embodiments, absorbent 164 can be provided in the form of a compact disk and is positioned on distal end 167 of the stem so that it is exposed and can be utilized to collect the sample from the individual who is being tested, for example, for the presence of drugs of abuse or other analytes.

In exemplary embodiments, for absorbing the sample fluid therein, absorbent 164 can comprise an untreated medical grade absorbent fiber sponge which will expand during the collection process. If desired, more than one sponge may be used with sample collector 160. Absorbent 164 can comprise, for example, a material selected from a sponge, cotton, cellulose, polyvinyl acetate (PVA), and hydrophilic polymers that expand as they wet. In exemplary embodiments, the sample fluid absorbed within the absorbent can be saliva, blood, urine, cerebrospinal fluid, nasal fluid, buccal cavity fluid, swab, tears, sweat, vaginal secretions, ear wax, or any other substance that is suitable for performing a desired testing procedure.

As shown in FIGS. 1 and 4-6, sample collector 160 is configured to be inserted from distal end 167 into housing 102 via second opening 114 of body portion 110 such that the distal end extends through the second opening to dispose absorbent 164 within reaction well 134 of mixing chamber 132. As explained in greater detail below, sample collector 160 is further configured to, upon being inserted into housing 102 via second opening 114, introduce a sample fluid absorbed within absorbent 164 to reaction well 134.

Body portion 110 is formed with a cylindrical bore 118 that longitudinally extends from a top 104 of housing 102 through an interior of the body portion to second opening 114 to be in fluid communication with mixing chamber 132 via the second opening at a bottom end 120 of the cylindrical bore. Body portion 110 is configured to slidably receive sample collector 160 in the cylindrical bore to allow for distal end 167 of the sample collector to be inserted into reaction well 134 via second opening 114.

Referring again to FIGS. 9a and 9b, sample collector 160 includes a generally cylindrical handle 170 formed with a hollow internal cavity 171 and includes at least one fastener 172 that is internally positioned within the cavity for retaining stem 162. Stem 162 is constructed to fit slidably within internal cavity 171 so that handle 170 can slide downward over the stem and, as described in greater detail below, cause absorbent 164 to express the sample fluid. Stem 162 is provided with a plurality of external protrusions 178 that allow for the at least one fastener 172 internally positioned in internal cavity 171 to retain handle 170 in a latched position in any of a plurality of positions upon the handle being moved downward over the stem to be placed in one these positions. In exemplary embodiments, handle 170 and stem 162 can be made from any suitable sturdy and sterilizable material such as hard plastic.

In exemplary embodiments, sample collector 160 may further include one or more breakable pegs that are configured to maintain stem 162 at an initial position relative to handle 170 within internal cavity 171 and constructed to break upon a depressing force being exerted on handle 170, which thereby allows for stem 162 to be released from the initial position and enable the handle to be downwardly slidable over the stem.

In the present exemplary embodiment, handle 170, at a distal end 174 thereof, is configured to apply compression to absorbent 164 retained on distal end 167 of stem 162 upon the handle being moved downward over the stem and impinging upon the absorbent from above to thereby cause the sample fluid absorbed within the absorbent to be expelled. More specifically, sample collector 160 includes a cylindrical foot portion 168 at distal end 167 of stem 162 upon which absorbent 164 is mounted so as to be retained on the stem between the foot portion and handle 170. Foot portion 168 is configured to abut against an interior surface of bottom section 144 of base portion 130 below second opening 114 when sample collector 160 is inserted from distal end 167 into housing 102 via the second opening such that absorbent 164 is disposed within reaction well 134 when the foot portion abuts against the bottom section. Upon handle 170 being moved downward over stem 162 when foot portion 168 is abutted against the interior surface of bottom section 144, the handle and the foot portion operate in conjunction to apply uniaxial compression to absorbent 164 to thereby expel the sample fluid absorbed within the absorbent to reaction well 134. Application of this compression to absorbent 164 can thereby operate to maximize the extraction of the sample fluid from the absorbent located at distal end 167 of sample collector 160.

As illustrated in FIGS. 9a and 9b, handle 170 can be constructed in two pieces or halves 170a and 170b that can be connected with one another to form the handle. Each half of handle 170 is formed with an internal channel such that the two internal channels form internal cavity 171 of handle 170 when the two halves are mated. Halves 170a and 170b may be joined in any suitable manner, such as, for example, use of corresponding pegs and holes 176, as shown in FIG. 9b. In exemplary embodiments, handle 170 can include a latching means that will allow the handle to be locked in position when compression of absorbent 164 is desired to express the sample fluid. In the present exemplary embodiment, distal end 174, which is the portion of handle 170 used for applying compression to the absorbent 164, has a larger circumference than a central portion of the handle.

Stem 162 is generally cylindrical and sized to fit slidably into internal cavity 171 of handle 170. Stem 162 is formed with a tapered end 163 opposite distal end 167 that fits inside handle 170, and foot portion 168 is formed at the distal end as a flange or flat disk that remains outside of the handle. As described above, foot portion 168 provides a supporting surface for absorbent 164 to be compressed when handle 170 is brought down onto the absorbent. External protrusions 178 of stem 162 are provided at a suitable location away from distal end 167 and constructed to be latched or otherwise retained by the at least one fastener 172 in internal cavity 171 of handle 170 after the handle is brought down upon the absorbent 164 so as to express the sample fluid such that the at least one fastener 172 will lock one of the protrusions in the stem to maintain the compressive force on the absorbent and maximize the expression of the sample fluid into reaction well 134. In the present exemplary embodiment, the stem includes a plurality of protrusions 178 to thereby provide for multiple latching positions.

In exemplary embodiments of the present invention, to carry out a testing procedure, stem 162 is swabbed in the subject at the appropriate location for the desired body fluid (for example, the interior of the mouth or nose of a potential testing subject), so that absorbent 164 at distal end 167 of the stem will absorb the body fluid from the subject. The collection of the body fluid can be conducted in a suitable manner appropriate to the particular body fluid that is to be tested. For example, where the fluid to be tested is saliva, tears, nasal fluid, ear wax or sweat, absorbent 164 may simply be swabbed on the appropriate area of the subject. In a saliva collection process, for instance, absorbent 164 may be placed between the cheek and gum of the subject for at least one minute, during which time the subject is instructed to avoid any chewing or sucking action. During this period, absorbent 164 will expand, reflecting the absorption of a suitable saliva sample, and this period can continue until the absorbent is fully expanded, thereby indicating that a suitable amount of saliva has been absorbed from the subject. Alternatively, where the fluid to be tested is blood or cerebrospinal fluid, it may generally be necessary to remove such fluids or otherwise make the fluid available to the sponge for testing. For blood, this may be accomplished, for instance, by venipuncture, and for cerebrospinal fluid, this may be accomplished, for instance, by a lumbar puncture. Accordingly, the testing procedure may vary depending on the nature of the bodily fluid desired to be tested.

At this point, with buffer agent 152 having been dispensed from buffer vial 150 and directed to reaction well 134 as described above, sample collector 160 can then be inserted from distal end 167 into housing 102 via second opening 114 of body portion 110 such that the distal end extends through the second opening to dispose absorbent 164 within reaction well 134 of mixing chamber 132. Upon insertion of sample collector 160 into housing 102 in this manner, buffer agent 152 will initially be absorbed into absorbent. As indicated above, the sample fluid and the absorbed buffer agent may be expressed from sample collector 160 by bringing the handle down towards absorbent 164 so that distal end 174 of handle 170 compresses the absorbent and the handle is brought into a locked position via the at least one fastener and the external protrusions of the stem. Prior to bringing handle 170 into a locked position, it may be useful to ensure that absorbent 164 is fully immersed in buffer agent with reaction well 134. After bringing handle 170 into a locked position, it may further be useful to rotate sample collector 160 to facilitate rinsing of absorbent 164 within reaction well to thereby assist in the expression of the sample from the absorbent.

Upon buffer agent 152 being dispensed from buffer vial 150 and directed to reaction well 134 and the sample fluid being introduced to the reaction well by sample collector 160, housing 102 allows for the buffer agent and the sample fluid to be mixed within the reaction well to form a test sample mixture within which absorbent 164 is immersed. Moreover, the configuration exemplary testing device 100 further allows for buffer agent 152 to operate to rinse the absorbent and provide for a more complete and precise mixing of the buffer agent with the sample fluid in the reaction well to form the test sample mixture. In exemplary embodiments, this rinsing operation can be aided by imparting energy to buffer agent 152 within reaction well 134 after the sample fluid has been introduced to the reaction well. For example, energy can be imparted to the buffer agent and the sample fluid in the reaction well when forming the test sample mixture by agitating or shaking housing 102 in a suitable manner with the reaction well 134 sealed, by way of initiating a suitable chemical reaction for this purpose within reaction well 134, or by any other suitable mechanism for providing energy to assist in the breakdown of the sample. Such action of imparting energy to the buffer solution and the test sample can operate to further assist in preparing the sample for the immunological testing, such as by breaking down mucins when the sample is saliva, or otherwise reducing the viscosity of the body fluid sample by removing or denaturing interferants, which will improve the ability of the test sample mixture to be tested in a lateral flow or other immunoassay.

In the present exemplary embodiment, as best illustrated in FIGS. 1-4, test strip holder 180 is constructed as a cassette having a sample receiving end 184 that holds test strip 182. Body portion 110 of housing 102 is configured to receive sample receiving end 184 of test strip holder 180 in third opening 116 and support the test strip holder outside of reaction well 134 until a time at which the immunoassay will be conducted. When it is time for the test to be conducted, for example upon the test sample mixture being formed within reaction well 134 following a suitable time for incubation of the test sample in buffer agent 152 in reaction well 134, body portion 110 is configured to allow for test strip holder 180 to be brought downward within third opening 116 so that test strip 182 is brought into communication with the text sample mixture in the reaction well to allow for the test to be conducted.

More specifically, body portion 110 is configured to slidably receive sample receiving end 184 of test strip holder 180 in third opening 116 and retain the test strip holder in a first position in which test strip 182 is not brought into communication with the test sample mixture in reaction well 134. When test strip holder 180 is retained in third opening 116, the test strip holder is supported adjacent to cylindrical bore and extends vertically in a parallel relationship with cylindrical bore 118. Upon test strip holder 180 being retained in the first position, body portion 110 is configured to allow for a depressing force to be exerted on the test strip holder for moving the test strip holder downward through third opening 116 from the first position to a second position at which test strip 182 is in communication with the test sample mixture in reaction well 134.

In exemplary embodiments, body portion 110 can be configured to further include a manually operated trigger that protrudes outwardly of the upper housing and can be pressed when desired to run the test to cause depressing force to be automatically exerted on test strip holder 180 and thereby move the test strip holder downward through third opening 116 from the first position to a second position. In alternative exemplary embodiments, testing device 100 may be configured to provide for test strip 182 to be brought in communication with the test sample mixture in reaction well 134 by other suitable mechanisms such as, for example, by the removal of a barrier or membrane, or opening of a valve, disposed between the reaction well and test strip holder 180 supported in third opening 116.

At least one vent 183 is formed at sample receiving end 184 of test strip holder 180 that opens into a narrow cavity 196 formed within test strip holder that is configured to enable test strip 182 to be brought into communication with the test sample mixture in reaction well 134 by way of capillary action of the test sample mixture within the narrow cavity upon the vent being brought into fluid communication with the test sample mixture in the reaction well. Test strip 182 will thereby operate via lateral flow so as to identify the presence and/or level of a target drug or analyte in the sample, which can be performed at a high level of sensitivity due to the removal of interfering particles in the text sample mixture.

As will be well understood by one of ordinary skill in the art, the immunoassay system may involve a suitable immunological identifying reagent such as a gold particle attached to a suitable antibody or antigen which can be used to target a particular drug of abuse or other analyte, and these materials are utilized in conjunction with test strip 182 wherein the test fluid moves through the strip via capillary action, and the presence of a desired analyte is determined by the presence of the identifying reagent at a suitable location down the test strip. In general, the identifying reagent will include a detectable component, for example, a magnetic particles, latex, colloidal silver, colloidal gold, charcoal, a fluorescent label, etc., and this identifying reagent will be bound to a material that can bind the target analyte, for example, an antibody, an antigen, a protein, a peptide, or any other suitable carrier molecule that can bind to the target analyte. As indicated herein, this identifying reagent may thus comprise a colloidal gold particle bound to an antibody, but many suitable identifying reagents and target-binding materials well known for this purpose may be utilized in accordance with exemplary embodiment of the present invention.

Test strips of the type that are suitable for use in exemplary embodiments of the present invention are well known in the art and are described, for example, in U.S. Patent Application Publication No. 2001/0012637, the content of which is incorporated herein by reference thereto. In general, these test strips may be of the type made by companies such as Inverness Medical of Switzerland, Pharmatech of San Diego, Calif. and Arista Biological of Bethlehem, Pa. Such test strips are characterized as immunoassay strips and employ an identifying reagent based on colloidal gold chemistry. These test strips are configured so as to conduct a lateral flow immunoassay when one end is brought into contact with a test mixture solution and can, for instance, allow for results of the test to be read in a test area coinciding with a visual opening in a testing device. As indicated above, these test strips can indicate the presence or absence of drugs of abuse including amphetamines, benzodiazepines, cocaine, methadone, methamphetamines, opiates, phencyclidine, PCP and THC, or other analytes when so desired.

In the present exemplary embodiment, when test strip holder 180 is inserted in third opening 116 and thereby retained by body portion 110 either the first or second portion, a first side 186 of the test strip holder faces a longitudinally extending exterior wall 122 of the body portion adjacent to cylindrical bore 118. When test strip holder 180 is retained in the second position, a top end 190 of the test strip holder extends longitudinally outward from third opening 116 toward top 104 of the housing 102 such that a test result portion 192 of the test strip holder from which reactions on the test strip can be observed is disposed above the third opening on a second side 188 of the test strip holder opposite first side 186.

Second side 188 of test strip holder 180 has an opening or viewing window 194 formed therein that allows a user to visually observe test result portion 192 from an exterior of housing 102 and thereby determine a presence or absence of a substance in the sample fluid based on a visual indication provided by the test result portion.

In exemplary embodiments, in addition to providing a visual mechanism for determining the presence or absence of the drug or analyte being tested, test strip 182 may also provide a visible means for evidencing that the test has been successfully conducted—that is, indicating that the lateral flow process has been completed and is valid to the person reading the test results. Test strip holder 180 can be configured, for example, so that this indication can also be viewed through viewing window 194 in second side 188 of the test strip holder. In exemplary embodiments, test strip holder 180 may be made of any suitable material such as metal or thermoplastic material using, for instance, embossing or injection molding.

Accordingly, exemplary embodiments of the present invention can be implemented to provide methods and devices that allow for quick, safe, and accurate testing of drugs of abuse or other analytes from a variety of body fluids including saliva, which can be used conveniently and effectively in a wide variety of settings, including on-the-spot testing, and which can be inexpensively manufactured with microfluidic features that provide or control sample preparation, flow rate, mixing with reagents, reaction time associated with binding events, filtration of nonanalytical components of the sample, separation of interfering agents and of multiple analytes, and an effective measurement capability.

In the preceding description, for purposes of explanation, numerous specific details are set forth in order to provide a thorough understanding of the described exemplary embodiments. Nevertheless, one skilled in the art will appreciate that many other embodiments may be practiced without these specific details and structural, logical, and electrical changes may be made.

Although exemplary embodiments of the present invention have been described in detail, the present description is not intended to be exhaustive or limiting of the invention to the described embodiments. It should be understood that various changes, substitutions and alterations could be made thereto without departing from spirit and scope of the inventions as defined by the appended claims. Variations described for exemplary embodiments of the present invention can be realized in any combination desirable for each particular application. Thus particular limitations, and/or embodiment enhancements described herein, which may have particular advantages to a particular application, need not be used for all applications. Also, not all limitations need be implemented in methods, systems, and/or apparatuses including one or more concepts described with relation to exemplary embodiments of the present invention.

Therefore, it is intended that the invention not be limited to the particular embodiments disclosed presented herein, which were chosen and described to best explain the principles of the present invention and the practical application, and to enable others of ordinary skill in the art to understand the invention. It will be understood that those skilled in the art, both now and in the future, may make various modifications to the exemplary embodiments described herein without departing from the spirit and the scope of the present invention as set forth in the following claims, wherein reference to an element in the singular, such as by use of the article "a" or "an" is not intended to mean "one and only one" unless specifically so stated, but rather "one or more." Moreover, no claim element is to be construed under the provisions of 35 U.S.C. §112, sixth paragraph, unless the element is expressly recited using the phrase "means for" or "step for." These following claims should be construed to maintain the proper protection for the present invention.

What is claimed is:

1. A lateral flow immunoassay system, comprising:
a housing that includes a body portion and a base portion having a first chamber formed within an interior of the base portion, the body portion being formed with first, second, and third openings in fluid communication with the first chamber;
a vial containing a buffer agent therein and mounted to the housing such that a dispensing side of the vial extends into the first opening of the body portion from an exterior of the housing to be in fluid communication with the first chamber, the vial being formed of a deformable material configured to dispense the total volume of a predetermined amount of the buffer agent from the dispensing side into the first chamber in response to a compressing force being exerted on an exterior surface of the vial; and
a sample collector comprising an absorbent material configured to introduce a sample fluid into the first chamber via the second opening of the housing and configured so that compression is applied to the sample collector so as to maximize the extraction of the sample from the absorbent material; and
wherein, upon the buffer agent being dispensed from the vial and the sample fluid being introduced to the first chamber, the housing allows for the buffer agent and the sample fluid to be mixed within a reaction well formed within the first chamber of the base portion to form a test sample mixture therein,
wherein the body portion is configured to receive a sample receiving end of an elongated holder member securing at least one immunoassay test strip therein in the third opening and support the holder member to allow for the test strip to be brought into communication with the test sample mixture upon the test sample mixture being formed within the reaction well,
wherein the absorbent material is fully immersed in the reaction well; and
wherein an immunological identifying reagent used to target an analyte of the sample is located on the test strip and not in the reaction well.

2. The lateral flow immunoassay system according to claim 1, wherein the base portion includes a reaction well formed within the first chamber in fluid communication with the second and third openings, wherein the reaction well is located beneath the second and third openings and positioned within the first chamber transversely separated from the first opening, and wherein the base portion is configured to, in response to the buffer agent being dispensed from the vial into the first chamber, direct the buffer agent to the reaction well.

3. The lateral flow immunoassay system according to claim 2, wherein an interior bottom surface of the base portion is formed with an inclined portion below the first opening that slopes transversely toward the reaction well for directing the buffer agent dispensed from the vial into the first chamber to flow by gravity into the reaction well of the first chamber.

4. The lateral flow immunoassay system according to claim 2, wherein the dispensing side of the vial comprises a rupturable end surface, wherein the base portion includes a piercing member protruding from an inner surface of the base portion within the first chamber such that a tip of the piercing member is in a facing spaced relationship with the first opening, wherein the piercing member is engageable with the rupturable end surface to form an aperture in the rupturable end surface, and wherein the vial is configured to, upon the aperture being formed in the dispensing side, dispense the buffer agent from the aperture in the dispensing side into the first chamber in response to the compressing force being exerted on the exterior of the vial.

5. The lateral flow immunoassay system according to claim 4, wherein the housing is configured to hold the vial at a first position spaced apart from the piercing member and to allow for a depressing force exerted on the vial to move the vial downward through the first opening to engage the rupturable end surface with the piercing member and thereby form the aperture.

6. The lateral flow immunoassay system according to claim 5, wherein the vial is mounted within the housing to allow for the depressing force to be manually exerted on a top surface of the vial opposite the dispensing side to move the vial downward through the first opening and to allow for the compressing force to be manually exerted by a squeezing action on the exterior of the vial.

7. The lateral flow immunoassay system according to claim 5, wherein the housing is configured to, in response to a button located on an exterior surface of the body portion being depressed, exert the depressing force to move the vial downward through the first opening.

8. The lateral flow immunoassay system according to claim 7, wherein the housing is configured to convert motion of the vial through the first opening into biaxial compression on the exterior of the vial to exert the compressing force on the exterior of the vial.

9. The lateral flow immunoassay system according to claim 1, wherein the vial possesses a modulus of elasticity that is determined so that the vial deforms elastically to totally dispense a predetermined amount of the buffer agent into the first chamber in response to the compressing force being exerted on an exterior of the vial.

10. A method for testing a sample fluid, the method comprising:

providing the lateral flow immunoassay system according to claim 1;

exerting a compressing force on an exterior of the vial to dispense the buffer agent from the dispensing side into the first chamber;

introducing a sample fluid from the sample collector into the first chamber via the second opening of the housing;

allowing for the buffer solution dispensed from the vial and the sample fluid introduced to the first chamber to be mixed within the reaction well formed within the first chamber to form a test sample mixture therein; and receiving the sample receiving end of the elongated holder member securing the at least one immunoassay test strip therein in the reaction well via the third opening of the body portion to bring the test strip into communication with the test sample mixture and initiate a test of the sample fluid.

11. The method according to claim 10, further comprising forming an aperture in the dispensing side through which the buffer agent is dispensed into the first chamber in response to the compressing force being exerted on the exterior of the vial.

12. The method according to claim 11, wherein the dispensing side of the vial comprises a rupturable end surface, wherein the base portion includes a piercing member protruding from an inner surface of the base portion within the first chamber such that a tip of the piercing member is in a facing spaced relationship with the first opening, wherein the piercing member is engageable with the rupturable end surface to form the aperture in the rupturable end surface, and further comprising holding the vial at a first position spaced apart from the piercing member and allowing for a depressing force exerted on the vial to move the vial downward through the first opening to engage the rupturable end surface with the piercing member and thereby form the aperture.

13. The method according to claim 10, wherein the reaction well is located beneath the second and third openings and positioned within the first chamber transversely separated from the first opening, and further comprising directing the buffer agent dispensed from the vial into the first chamber to the reaction well.

14. The method according to claim 13, wherein an interior bottom surface of the base portion is formed with an inclined portion below the first opening that slopes transversely toward the reaction well for directing the buffer agent dispensed from the vial into the first chamber to flow by gravity into the reaction well of the first chamber.

* * * * *